(12) United States Patent
Park et al.

(10) Patent No.: US 8,525,244 B2
(45) Date of Patent: Sep. 3, 2013

(54) GERMANIUM COMPOUND, SEMICONDUCTOR DEVICE FABRICATED USING THE SAME, AND METHODS OF FORMING THE SAME

(75) Inventors: Hye-Young Park, Gyeonggi-do (KR);
Myong-Woon Kim, Gyeonggi-do (KR);
Jin-Dong Kim, Gyeonggi-do (KR);
Choong-Man Lee, Seoul (KR); Jin-Il Lee, Gyeonggi-do (KR)

(73) Assignee: Samsung Electronics Co., Ltd. (KR)

( * ) Notice: Subject to any disclaimer, the term of this patent is extended or adjusted under 35 U.S.C. 154(b) by 933 days.

(21) Appl. No.: 11/777,854

(22) Filed: Jul. 13, 2007

(65) Prior Publication Data
US 2008/0035906 A1 Feb. 14, 2008

(30) Foreign Application Priority Data
Jul. 13, 2006 (KR) .................. 10-2006-0065987

(51) Int. Cl.
*H01L 27/108* (2006.01)

(52) U.S. Cl.
USPC ............ 257/298; 257/E31.026; 257/E31.029; 438/95; 427/255.31; 427/255.35

(58) Field of Classification Search
USPC ............... 257/214, 298, E31.001, E31.002, 257/E31.003, E31.004, E31.026, E31.029; 438/48, 57, 93, 95; 427/255.29, 255.31, 427/255.32, 255.35
See application file for complete search history.

(56) References Cited

U.S. PATENT DOCUMENTS

| 4,871,220 | A * | 10/1989 | Kohin ........................ 359/350 |
| 6,984,591 | B1 | 1/2006 | Buchanan et al. |
| 2003/0117155 | A1 * | 6/2003 | Horner et al. ............... 324/719 |
| 2004/0197945 | A1 | 10/2004 | Woelk et al. |
| 2004/0198042 | A1 | 10/2004 | Shenai-Khatkhate |
| 2004/0251551 | A1 | 12/2004 | Hideki |
| 2006/0001017 | A1 | 1/2006 | Chang |
| 2006/0049447 | A1 * | 3/2006 | Lee et al. ..................... 257/314 |
| 2006/0072370 | A1 * | 4/2006 | Kuh et al. ..................... 365/232 |
| 2009/0124039 | A1 * | 5/2009 | Roeder et al. .................. 438/99 |
| 2009/0305458 | A1 * | 12/2009 | Hunks et al. ................. 438/102 |

FOREIGN PATENT DOCUMENTS

| JP | 2001-172288 | 6/2001 |
| KR | 10-2004-0086801 | 10/2004 |
| KR | 10-2006-0008027 | 1/2006 |
| KR | 10-2006-0074236 | 7/2006 |
| TW | I314167 B | 9/2009 |
| TW | I318222 B | 12/2009 |

OTHER PUBLICATIONS

English language abstract of Korean Publication No. 10-2004-0086801.
English language abstract of Korean Publication No. 10-2006-0008027.

(Continued)

*Primary Examiner* — William D Coleman
*Assistant Examiner* — Su Kim
(74) *Attorney, Agent, or Firm* — Myers Bigel Sibley & Sajovec PA

(57) ABSTRACT

A germanium (Ge) compound is provided. The Ge compound has a chemical formula $GeR^1xR^2y$. "$R^1$" is an alkyl group, and "$R^2$" is one of hydrogen, amino group, allyl group and vinyl group. "x" is greater than zero and less than 4, and the sum of "x" and "y" is equal to 4. Methods of forming the Ge compound, methods of fabricating a phase change memory device using the Ge compound, and phase change memory devices fabricated using the Ge compound are also provided.

14 Claims, 5 Drawing Sheets

(56) References Cited

OTHER PUBLICATIONS

Soderquist et al. "Direct Synthesis of Metallacycloalkanones via the Cyclic Hydroboration of Dialkenyl Derivatives of Silicon, Germanium, and Tin" *Journal of Organic Chemistry*, vol. 48, pp. 1801-1810, 1983.

Akiyama et al. "Lewis acid mediated [3 +2] cycloaddition of allylgermane: stereoselective synthesis of germyl substituted tetrahydrofurans" *Chem. Commun.*, pp. 2357-2358, 1997.

* cited by examiner

GERMANIUM COMPOUND, SEMICONDUCTOR DEVICE FABRICATED USING THE SAME, AND METHODS OF FORMING THE SAME

CROSS-REFERENCE TO RELATED APPLICATION

This application claims the benefit of foreign priority to Korean Patent Application No. 10-2006-0065987, filed Jul. 13, 2006, the disclosure of which is hereby incorporated herein by reference in its entirety.

BACKGROUND

1. Field of Invention

Embodiments of the present invention relate generally to chemical compounds, semiconductor devices fabricated using such chemical compounds and methods of forming such semiconductor devices. More particularly, embodiments of the present invention relate to a germanium compound, a semiconductor device fabricated using the germanium compound and methods of fabricating such a semiconductor device.

2. Description of the Related Art

Volatile memory devices and nonvolatile memory devices are types of semiconductor devices. Data stored within volatile memory devices is lost when power is not supplied to the memory device. However, nonvolatile memory devices retain stored data even in the absence of power. Accordingly, nonvolatile memory devices have been widely used in memory cards, telecommunication systems and the like.

Nonvolatile memory devices include flash memory devices or phase change memory devices. Phase change memory devices are very attractive as next-generation memory devices to replace flash memory devices. Phase change memory devices typically include a phase change material that may exhibit one of at least two different phases—for example a crystalline phase and an amorphous phase. The phase of the phase change material may be changed into an amorphous phase or a crystalline phase according to a heating temperature applied thereto and a quenching process of the heated phase change material. The phase change material having the crystalline phase exhibits a relatively low electrical resistance and phase change material having the amorphous phase exhibits a relatively high electrical resistance.

FIG. 1 is a cross sectional view illustrating a fabrication method of a conventional phase change memory device.

Referring to FIG. 1, an insulating layer 30 is formed on a substrate 10 having a lower interconnection 20. The insulating layer 30 is patterned to form an opening 35 and a lower electrode 40 is formed in the opening 35. A phase change material layer and an upper electrode layer are sequentially formed on the lower electrode 40 and the insulating layer 30. Each of the phase change material layer and the upper electrode layer may be formed using a physical vapor deposition technique such as a sputtering method. The upper electrode layer and the phase change material layer are then patterned using a conventional photolithography process and a conventional etching process to form a phase change material pattern 50 and an upper electrode 60, which are sequentially stacked on the lower electrode 40.

As phase change memory devices become more highly integrated, the width of the phase change material pattern 50 must be reduced. However, when the phase change material pattern 50 is formed using the photolithography process and the etching process as described above, there may be a limitation in reducing the size of the phase change material pattern 50. Accordingly, it may be difficult to form small phase change material patterns having a width less than about 100 nm using the conventional photolithography and etching processes. Further, if the width of the phase change material pattern 50 is greater than a width of the lower electrode 40, heat for changing the crystalline structure of the phase change material pattern 50 may be easily dissipated. Therefore, it is difficult to reduce power consumption, which is required to change the crystalline structure of the phase change material pattern 50.

Recently, another conventional method of fabricating phase change memory devices has been proposed to reduce the power consumption in a program mode. According to the other conventional method, an insulating layer is patterned to form an opening and a phase change material pattern is formed in the opening using a chemical vapor deposition (CVD) technique. However, when the phase change material pattern is formed in the opening using conventional CVD techniques, the phase change material pattern may be non-uniformly formed within the opening.

SUMMARY

Embodiments exemplarily described herein can be generally characterized as being directed to a germanium compound useful in forming a substantially uniform layer and a method of forming the same. Also, embodiments exemplarily described herein can be generally characterized as being directed to semiconductor devices and methods of forming the same using the germanium compound.

One embodiment exemplarily described herein can be characterized as a germanium compound having a chemical formula $GeR^1_x R^2_y$. "$R^1$" is an alkyl group, and "$R^2$" is one of hydrogen, an amino group, an allyl group and a vinyl group. "x" is greater than zero and less than 4, and sum of "x" and "y" equal to 4. In one embodiment, "$R^1$" may comprise iso-propyl. In another embodiment, the amino group may comprise $NR^3R^4$, and each of "$R^3$" and "$R^4$" may be an alkyl group. In yet another embodiment, "$R^3$" may be one of methyl, ethyl, iso-propyl and tert-butyl, and "$R^4$" may be one of methyl, ethyl, iso-propyl and tert-butyl.

Another embodiment exemplarily described herein can be characterized as a method of forming a germanium compound that includes reacting tetra halide germanium $GeX^1_4$ with a first chemical compound having a chemical formula $R^1MgX^2$ to generate a second chemical compound having a chemical formula $GeR^1_x X^1_y$, and reacting the second chemical compound $GeR^1_x X^1_y$ with a third chemical compound having a chemical formula $LiR^2$ or a fourth chemical compound having a chemical formula $R^2MgX^3$ to generate a fifth chemical compound having a chemical formula $GeR^1_x R^2_y$. "$R^1$" is an alkyl group, and "$R^2$" is one of hydrogen, an amino group, an allyl group and a vinyl group. Each of "$X^1$", "$X^2$" and "$X^3$" may be a halogen element. "x" may be greater than zero and less than 4 and sum of "x" and "y" may be equal to 4. In one embodiment, the tetra halide germanium $GeX^1_4$ may be tetra chloro germanium $GeCl_4$. In another embodiment, "$R^1$" may include iso-propyl. In another embodiment, the amino group may be $NR^3R^4$, and each of $R^3$ and $R^4$ may be an alkyl group. "$R^3$" may be one of methyl, ethyl, iso-propyl and tert-butyl, and "$R^4$" may be one of methyl, ethyl, iso-propyl and tert-butyl.

Yet another embodiment exemplarily described herein can be characterized as a method of forming a semiconductor device that includes supplying a germanium precursor, an antimony precursor and a tellurium precursor toward a substrate to form a phase change material layer. The germanium precursor may be a germanium compound having a chemical formula GeR$^1_x$R$^2_y$. "R$^1$" may be an alkyl group and "R$^2$" may be one of hydrogen, an amino group, an allyl group and a vinyl group. "x" may be greater than zero and less than 4, and sum of "x" and "y" equal to 4. In one embodiment, "R$^1$" may comprise iso-propyl. In another embodiment, the amino group may comprise NR$^3$R$^4$, and each of "R$^3$" and "R$^4$" may be an alkyl group. "R$^3$" may be one of methyl, ethyl, iso-propyl and tert-butyl, and "R$^4$" may be one of methyl, ethyl, iso-propyl and tert-butyl. In another embodiment, the antimony precursor may be tri iso-propyl antimony (Sb(C$_3$H$_7$)$_3$). In another embodiment, the tellurium precursor may be tert butyl tellurium (Te(C$_4$H$_9$)$_2$). In another embodiment, the germanium precursor, the antimony precursor and the tellurium precursor may be supplied by periodically supplying a first source material containing the germanium precursor and the tellurium precursor and periodically supplying a second source material containing the antimony precursor and the tellurium precursor. The first and second source materials may be alternately supplied. In another embodiment, an insulating layer having an opening therein may be formed before forming the phase change material layer. In this case, the phase change material layer may be formed in the opening. The opening may have a width of about 100 nm or less. In addition, a conductive plug may be formed in the lower region of the opening before forming the phase change material layer. In still another embodiment, the phase change material layer may be formed by performing a chemical vapor deposition process or an atomic layer deposition process at a process temperature of about 250° C. to about 350° C. The process temperature may be equal to or lower than about 325° C.

A further embodiment exemplarily described herein can be characterized as a semiconductor device that includes a substrate including a conductive region and an insulating layer on the substrate. The insulating layer may include an opening that exposes the conductive region. A phase change material pattern may be located in the opening. A top surface of the phase change material pattern may be substantially coplanar with or lower than a top surface of the insulating layer. In one embodiment, the phase change material pattern may have a width of about 100 nm or less. In other embodiments, a conductive plug may be provided between the phase change material pattern and the conductive region. In yet other embodiments, a conductive pattern may be disposed on the phase change material pattern.

BRIEF DESCRIPTION OF THE DRAWINGS

Exemplary embodiments of the present invention can be understood in more detail from the following descriptions taken in conjunction with the accompanying drawings in which.

DETAILED DESCRIPTION

Figure 1:
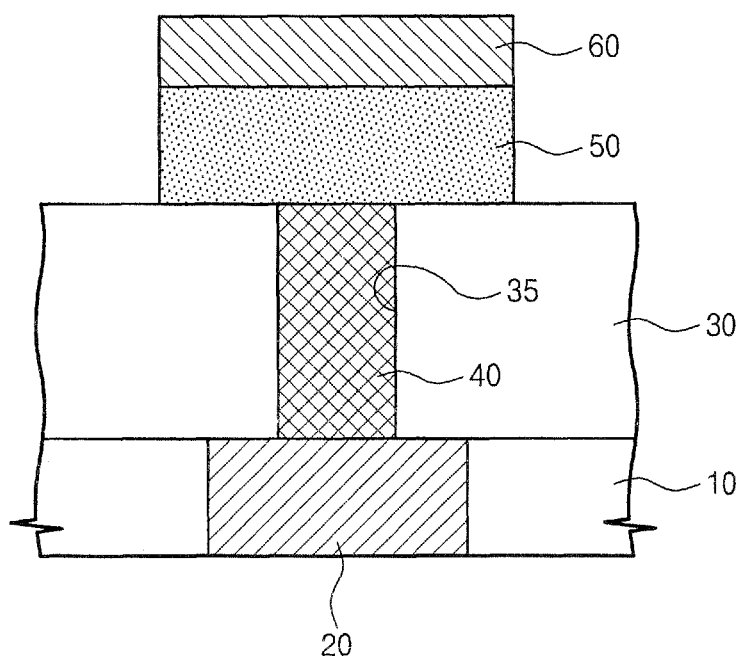
FIG. 1 is a cross sectional view illustrating a method of fabricating a conventional phase change memory device.

Exemplary embodiments of the present invention will now be described more fully with reference to the accompanying drawings. These embodiments may, however, be realized in different forms and should not be construed as limited to the embodiments set forth herein. Rather, these embodiments are provided so that this disclosure will be thorough and complete, and will fully convey the scope of the invention to those skilled in the art. Some embodiments can generally be characterized as being directed to a germanium compound and a method of forming the germanium compound. Other embodiments can generally be characterized as being directed to methods of forming phase change material patterns employed in semiconductor devices such as, for example, semiconductor memory devices.

(Germanium Compound)

According to some embodiments, a germanium compound can be characterized as having the following chemical formula 1.

GeR$^1_x$R$^2_y$     (chemical formula 1)

In chemical formula 1, "R$^1$" may be an alkyl group, and "R$^2$" may be one of hydrogen (H), an amino group, an allyl group and a vinyl group. Further, "x" may be greater than zero and less than four and the sum of "x" and "y" may be four. In some embodiments, "x" and "y" may be natural numbers. For example, paired values for ("x", "y") may be (1, 3), (2, 2) or (3, 1). In one embodiment, when "y" is greater than 2, all of "R$^2$" may be the same atomic group or at least one of "R$^2$" may be a different atomic group from the others. For example, when "x" is 1 and "y" is 3, the germanium compound may be expressed as GeR$^1$R$^2_3$. In this case, all of three "R$^2$" may be selected from the same atomic group or the three "R$^2$" may be selected from three different atomic groups. Alternatively, two of three "R$^2$" may be selected from the same atomic group and one remainder thereof may be a different atomic group from the two "R$^2$".

In the germanium compound, "R$^1$" may include, for example, iso-propyl. In one embodiment, "R$^1$" may be iso-propyl. The amino group may be expressed by a chemical formula NR$^3$R$^4$, and "R$^3$" and "R$^4$" may be the alkyl group. For example, each of "R$^3$" and "R$^4$" may be one selected from the group consisting of methyl, ethyl, iso-propyl and tert-butyl. "R$^3$" and "R$^4$" may be the same atomic group, or "R$^3$" and "R$^4$" may be different atomic groups from each other.

In some embodiments, the germanium compound may be one of iso-propyl germanium (GeH$_3$(iso-C$_3$H$_7$)), iso-propyl tris-methylethylamino germanium (Ge(iso-C$_3$H$_7$)(N(CH$_3$)(C$_2$H$_5$))$_3$), iso-propyl tri-allyl germanium (Ge(iso-C$_3$H$_7$)(C$_3$H$_5$)$_3$), iso-propyl tri-vinyl germanium (Ge(iso-C$_3$H$_7$)(C$_2$H$_3$)$_3$), di-iso-propyl germanium (GeH$_2$(iso-C$_3$H$_7$)$_2$), di-iso-propyl bis-methylethylamino germanium (Ge(iso-C$_3$H$_7$)$_2$(N(CH$_3$)(C$_2$H$_5$))$_2$), di-iso-propyl di-allyl germanium (Ge(iso-C$_3$H$_7$)$_2$(C$_3$H$_5$)$_2$), di-iso-propyl di-vinyl germanium (Ge(iso-C$_3$H$_7$)$_2$(C$_2$H$_3$)$_2$), tri-iso-propyl germanium (GeH(iso-C$_3$H$_7$)$_3$), tri-iso-propyl methylethylamino germanium (Ge(iso-C$_3$H$_7$)$_3$(N(CH$_3$)(C$_2$H$_5$))), tri-iso-propyl allyl germanium (Ge(iso-C$_3$H$_7$)$_3$(C$_3$H$_5$)) and tri-iso-propyl vinyl germanium (Ge(iso-C$_3$H$_7$)$_3$(C$_2$H$_3$)). It will be appreciated, however, that the germanium compound is not necessarily limited to the above materials. That is, the germanium compound may have diverse chemical formulas according to the atomic group selected from the group consisting of $R^1$, $R^2$, $R^3$ and $R^4$.

In some embodiments, the aforementioned germanium compound may be used as a germanium precursor in a thin film deposition process. For example, the germanium compound may be used as a germanium (Ge) precursor during formation of a phase change material layer such as a germanium antimony tellurium (GeSbTe) layer to be used, for example, in a semiconductor device (e.g., a semiconductor memory device such as a phase change memory device). In embodiments where the aforementioned germanium compound is used as a Ge precursor, the phase change material layer may be uniformly formed even at a low temperature below about 350° C. In such embodiments, the phase change material layer may be uniformly formed at a temperature ranging between, for example, about 250° C. and about 350° C.

(Methods of Forming a Germanium Compound)

In one embodiment, a germanium compound may be formed in a two-step process using tetra halide germanium ($GeX^1_4$). As used herein, a compound having a chemical formula $GeR^1_xR^2_y$ is referred to as a "first compound", a compound having a chemical formula $R^1MgX^2$ may be referred to as a "second compound", a compound having a chemical formula $GeR^1_xX^1_y$ may be referred to as a "third compound", a compound having a chemical formula $LiR^2$ may be referred to as a "fourth compound", and a compound having a chemical formula $R^2MgX^3$ may be referred to as a "fifth compound". Although the terms first, second, etc. may be used herein to describe various compounds, these compounds should not be limited by these terms. These terms are only used to distinguish one compound from another compound. In the chemical formulas, "$R^1$" may be an alkyl group, "$R^2$" may be one of hydrogen (H), an amino group, an allyl group and a vinyl group, and each of "$X^1$", "$X^2$" and "$X^3$" may be a halogen element. Here, "x" may be greater than zero and less than four, and sum of "x" and "y" may be four. In this case, "x" and "y" may be natural numbers. For example, a pair of "x" and "y" may be (1, 3), (2, 2) or (3, 1). The first compound ($GeR^1_xR^2_y$) indicates the germanium compound.

To form the germanium compound, the tetra halide germanium ($GeX^1_4$) may be reacted with the second compound ($R^1MgX^2$) to generate the third compound ($GeR^1_xX^1_y$). This reaction corresponds to a first reaction. In one embodiment, "$X^1$" may be chlorine (Cl) and the second compound ($R^1MgX^2$) may be a Grignard compound having an atomic group "$R^1$". For example, "$R^1$" may be iso-propyl, and "$X^2$" may be bromine (Br). The first reaction may replace a portion of the "$X^1$" component in the tetra halide germanium ($GeX^1_4$) with "$R^1$" of the second compound ($R^1MgX^2$). In this case, one mole of the tetra halide germanium ($GeX^1_4$) may react with "x" moles of the second compound ($R^1MgX^2$), thereby generating one mole of the third compound ($GeR^1_xX^1_y$). The first reaction may be expressed by the following reaction formula 1.

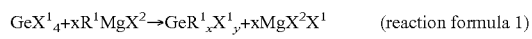  (reaction formula 1)

The third compound ($GeR^1_xX^1_y$) may react with the fourth compound ($LiR^2$) or the fifth compound ($R^2MgX^3$) to generate the first compound ($GeR^1_xR^2_y$). This reaction corresponds to a second reaction. The fourth compound ($LiR^2$) may be a lithium compound, and the fifth compound ($R^2MgX^3$) may be a Grignard compound. The fourth compound ($LiR^2$) and the fifth compound ($R^2MgX^3$) have an atomic group $R^2$. In one embodiment, "$R^2$" is an amino group that may, for example, include atomic groups "$R^3$" and "$R^4$", wherein "$R^3$" and "$R^4$" may be an alkyl group. For example, each of "$R^3$" and "$R^4$" may be one of methyl, ethyl, iso-propyl and tert-butyl. In this case, "$R^3$" and "$R^4$" may be the same or different from each other. Further, "$X^3$" may be bromine (Br). The second reaction may replace the remaining "$X^1$" component (i.e., the remaining halogen element that was not replaced during the first reaction) of the third compound ($GeR^1_xX^1_y$) with "$R^2$" of the fourth compound ($LiR^2$) or "$R^2$" of the fifth compound ($R^2MgX^3$). In this case, one mole of the third compound ($GeR^1_xX^1_y$) may react with "y" moles of the fourth compound ($LiR^2$) or "y" moles of the fifth compound ($R^2MgX^3$), thereby generating one mole of the first compound ($GeR^1_xR^2_y$). The second reaction may be expressed by the following reaction formula 2A or 2B.

  (reaction formula 2A)

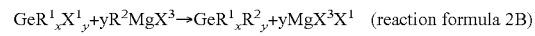  (reaction formula 2B)

(Semiconductor Devices and Methods of Forming the Same)

FIGS. 2 to 5 are cross sectional views illustrating an exemplary method of forming a phase change memory device according to one embodiment. As used herein, the term "phase change memory device" denotes all semiconductor devices that include a phase change material layer as a data storage element. It will also be understood that when a layer is referred to as being "on" another layer or substrate, it can be directly on the other layer or substrate, or intervening layers may also be present. In the drawings, the thickness of layers and regions may be exaggerated for clarity.

Figure 2:
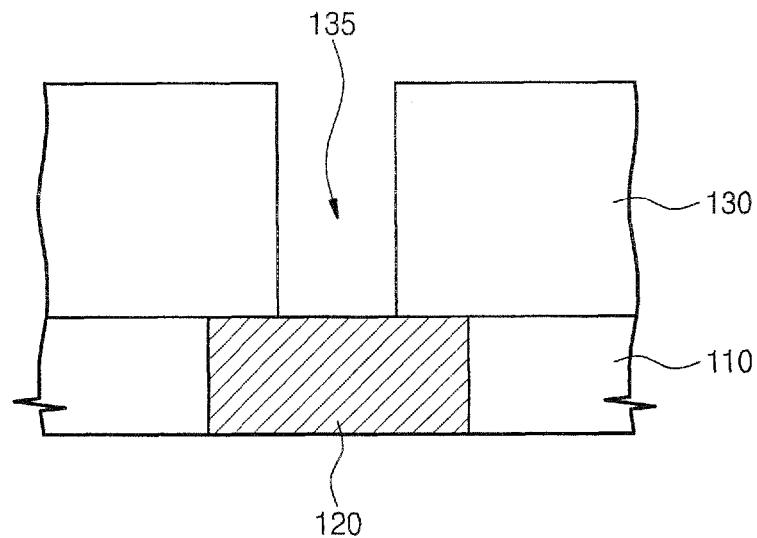
FIGS. 2 to 5 are cross sectional views illustrating an exemplary method of fabricating a semiconductor device according to one embodiment.

Referring to FIG. 2, an insulating layer 130 may be formed on a substrate 110 having a conductive region 120. An opening 135 may be defined within the insulating layer 130 that exposes the conductive region 120. In one embodiment, the insulating layer 130 may be patterned to form the opening 135. A width of the opening 135 may be substantially equal to 100 nm or may be less than about 100 nm.

Figure 3:
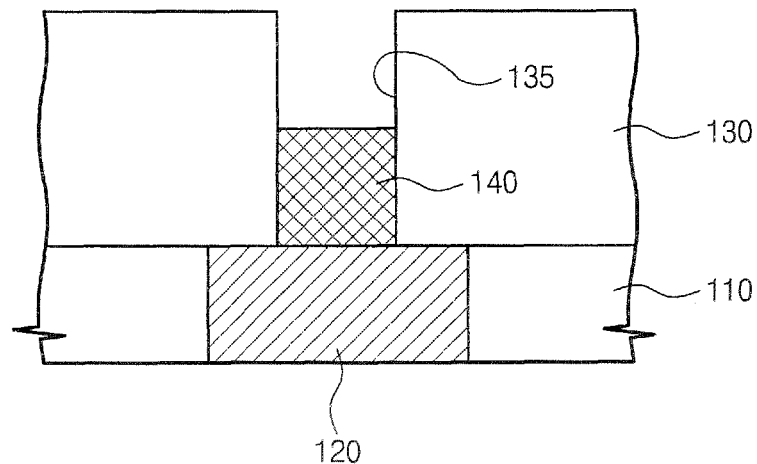

Referring to FIG. 3, a conductive plug 140 may be formed in a lower portion of the opening 135. In one embodiment, the conductive plug 140 may be formed by, for example, substantially completely filling the opening 135 with a conductive material layer and then recessing the conductive material layer.

Figure 4:
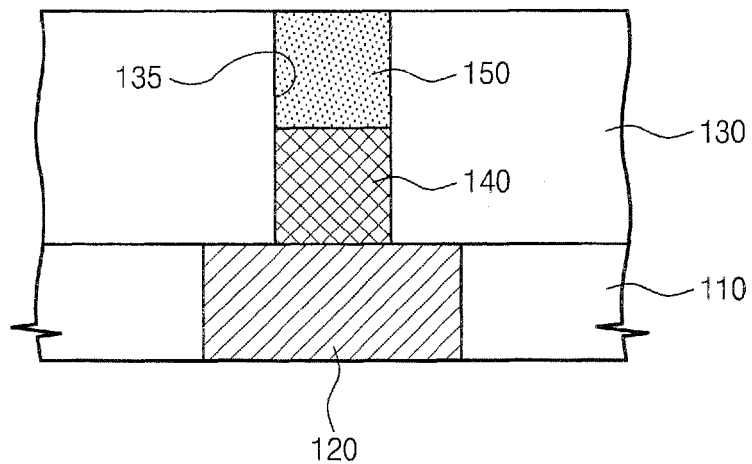

Referring to FIG. 4, a phase change material layer may be formed on the substrate 110 having the conductive plug 140 and the phase change material layer may then be planarized until a top surface of the insulating layer 130 is exposed. As a result, a phase change material pattern 150 may be formed in the opening 135 and on the conductive plug 140. Therefore, the phase change material pattern 150 may have the substantially same width as the opening 135. For example, the phase change material pattern 150 may have a width that is substantially 100 nm or less than about 100 nm. Further, a top surface of the phase change material pattern 150 may be substantially coplanar with a top surface of the insulating layer 130 or may be lower than the top surface of the insulating layer 130.

The phase change material layer may be formed using a chemical vapor deposition (CVD) technique or an atomic layer deposition (ALD) technique that employs a germanium (Ge) precursor, an antimony (Sb) precursor and a tellurium (Te) precursor as source materials. Thus, a GeSbTe layer (e.g., a $Ge_2Sb_2Te_5$ layer) containing germanium (Ge), antimony (Sb) and tellurium (Te) may be formed on the substrate 110 having the conductive plug 140. The Ge precursor may be the germanium compound expressed by the aforementioned chemical formula 1.

In some embodiments, the phase change material layer may be formed at a low temperature below about 350° C. and may be formed to have a dense and substantially uniform structure. In such embodiments, the phase change material layer may be formed at a temperature ranging between, for example, about 250° C. and about 350° C. Further, the phase change material pattern 150 may be formed to have a width less than about 100 nm, without use of a photolithography process. Thus, it is possible to reduce a program current which is required to change the crystalline structure of the phase change material pattern 150 and to improve the integration density of the phase change memory device. As a result, it can be easy to realize a high performance phase change memory device that exhibits low power consumption characteristic with high integration density.

Figure 5:
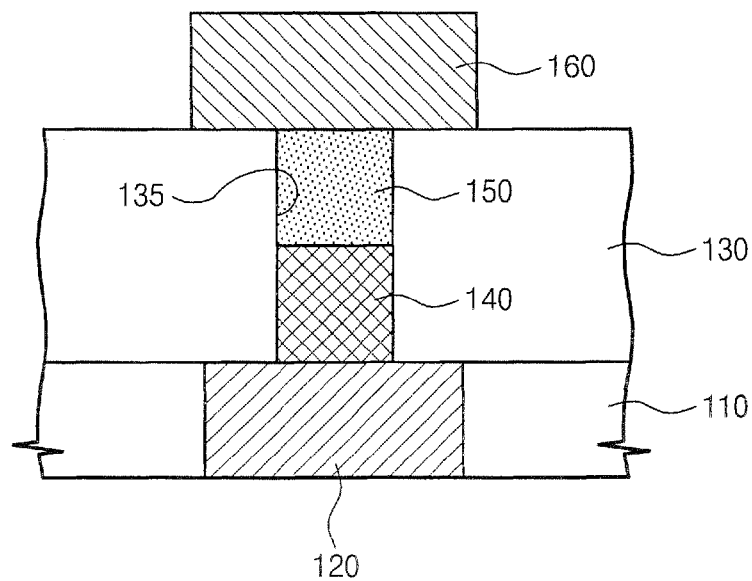

Referring to FIG. 5, a conductive pattern 160 may be formed on the phase change material pattern 150. In one embodiment, the conductive region 120, the conductive plug 140, the phase change material pattern 150 and the conductive pattern 160 may act as a lower interconnection, a lower electrode (or a heating electrode), a data storage layer and an upper electrode, respectively. The conductive region 120 may be electrically connected to, for example, a source region (or a drain region) of a metal-oxide-semiconductor (MOS) transistor formed thereunder. The conductive pattern 160 may be electrically connected to, for example, an interconnection (not shown) formed thereabove. The conductive region 120 may, for example, include molibdenum (Mo) or tungsten (W), and the conductive pattern 160 may include titanium nitride (TiN), tantalum nitride (TaN) tungsten nitride (WN), or the like or a combination thereof.

Exemplary methods of forming the germanium compound, and exemplary methods of forming the phase change memory device, will now be described with respect to Embodiment 1 and Embodiment 2 below.

(Embodiment 1)

In Embodiment 1, a germanium compound may be formed by first reacting about 3.5 moles of magnesium and about 3.1 moles of isopropyl bromine with each other in about 3 liters of ethyl ether for two hours and removing unreacted magnesium to provide an isopropyl bromomagnesium ((iso-$C_3H_7$)MgBr) solution. Tetra-chloro germanium ($GeCl_4$) may then be added into the isopropyl bromomagnesium ((iso-$C_3H_7$)MgBr) solution and the tetra-chloro germanium ($GeCl_4$) and the isopropyl bromomagnesium ((iso-$C_3H_7$)MgBr) may then be reacted with each other at a temperature of about 130° C. for about 12 hours. In one embodiment, the isopropyl bromomagnesium ((iso-$C_3H_7$)MgBr) solution may be refluxed with the tetra-chloro germanium ($GeCl_4$) during the reaction. The reaction of the isopropyl bromomagnesium ((iso-$C_3H_7$)MgBr) and the tetra-chloro germanium ($GeCl_4$) may be expressed by the following reaction formula 3.

$$GeCl_4 + (iso\text{-}C_3H_7)MgBr \rightarrow Ge(iso\text{-}C_3H_7)Cl_3 + MgBrCl$$
(reaction formula 3)

The solution generated by the reaction formula 3 may be filtered using a filter to obtain a filtrate. A solvent in the filtrate may be removed at room temperature in a vacuum to obtain a colorless liquid. The colorless liquid thus obtained may then be distilled in a vacuum to generate iso-propyl tri-chloro germanium (Ge(iso-$C_3H_7$)$Cl_3$).

About 3 moles of the iso-propyl tri-chloro germanium (Ge(iso-$C_3H_7$)$Cl_3$) may then be added into about 3 liters of ethyl ether having a temperature of about 130° C. to provide an iso-propyl tri-chloro germanium solution. About 9 moles of ethyl methyl amino lithium (LiN($C_2H_5$)($CH_3$)) may be added to the iso-propyl tri-chloro germanium solution and reacted therewith for about 110 hours. This reaction may be expressed by the following reaction formula 4.

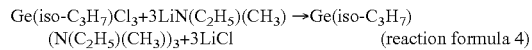
(reaction formula 4)

The solution generated by the reaction formula 4 may then be filtered using a filter to obtain a filtrate. A solvent in the filtrate may be removed at room temperature in vacuum to obtain a colorless liquid. The colorless liquid thus obtained may be distilled in a vacuum to generate iso-propyl tris ethyl methyl amino germanium (Ge(iso-$C_3H_7$)(N($C_2H_5$)($CH_3$))$_3$). In this reaction, a Grignard compound such as ethyl methyl amino bromo magnesium (N($C_2H_5$)($CH_3$)MgBr) may be used instead of the ethyl methyl amino lithium (LiN($C_2H_5$)($CH_3$)) corresponding to a lithium compound.

(Embodiment 2)

Figure 6:
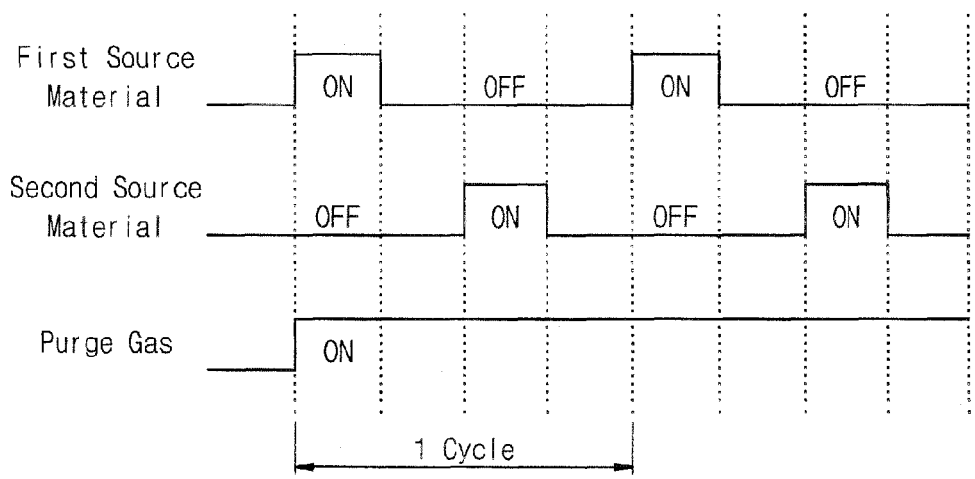
FIG. 6 is a timing diagram illustrating an exemplary method of forming a phase change material layer according to one embodiment.

FIG. 6 is a timing diagram to illustrate a method of forming a phase change material layer according to one embodiment.

Referring to FIG. 6, a Ge precursor, a Sb precursor and a Te precursor are provided on a substrate. The germanium compound (for example, Ge(iso-$C_3H_7$)(N($C_2H_5$)($CH_3$))$_3$) described above with respect to Embodiment 1 may be used as the Ge precursor, tri iso-propyl antimony (Sb($C_3H_7$)$_3$) may be used as the Sb precursor, and tert-butyl tellurium (Te($C_4H_9$)$_2$) may be used as the Te precursor.

In one embodiment, a first source material containing the Ge and Te precursors and a second source material containing the Sb and Te precursors may be alternately and repeatedly supplied to perform a chemical vapor deposition (CVD) process. Each of the first and second source materials may be supplied for about one second. A purge gas may be supplied during the CVD process. The purge gas may include, for example, argon (Ar) gas and hydrogen (H) gas. The CVD process may be performed at a process temperature of about 350° C. or lower and under a process pressure of about 5 Torr. In one embodiment, the CVD process may be performed at a process temperature ranging between about 250° C. and about 350° C. In another embodiment, the CVD process may be performed at a process temperature of about 325° C. It will be appreciated that the supply of the Ge precursor, the Sb precursor and the Te precursor is not limited to the method described above. For example, the Ge precursor, the Sb precursor and the Te precursor may be alternately and repeatedly supplied with one another. In other embodiments, the Ge precursor, the Sb precursor and the Te precursor may be simultaneously supplied.

According to the embodiments exemplarily described above, the phase change material layer may be uniformly formed at a low temperature of about 350° C. or lower. Thus, the phase change material layer may substantially fill even a narrow opening having a width of about 100 nm or less (e.g., 100 nm or less). As a result, a highly integrated phase change memory device may be realized using the embodiments exemplarily described above.

Figure 7:
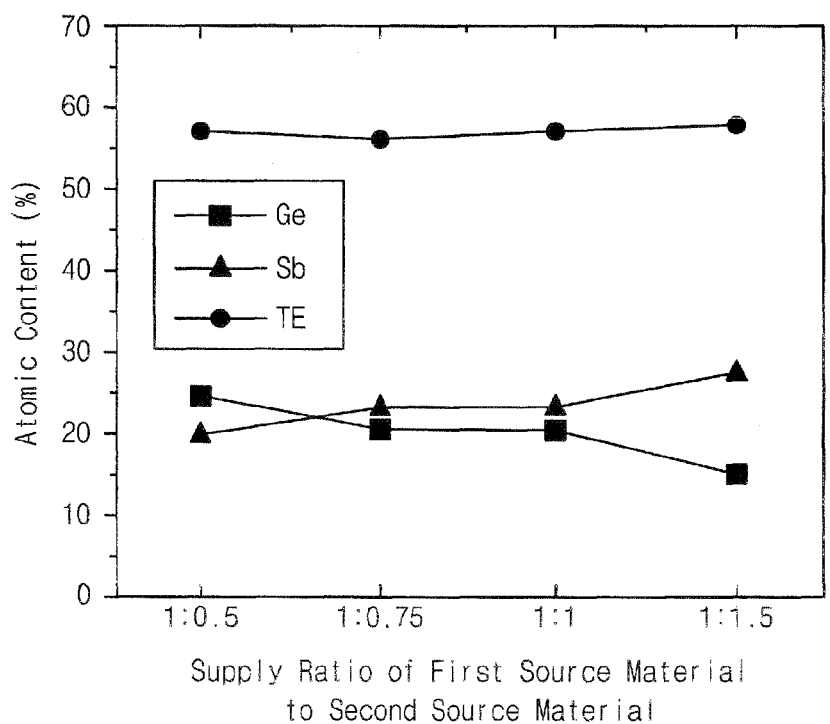
FIG. 7 is a graph illustrating relationships between composition ratios and process conditions of phase change material layers formed according to embodiments of the present invention.

FIG. 7 is a graph illustrating relationships between composition ratios and process conditions of phase change material layers formed according to embodiments exemplarily described above. As shown in FIG. 7, the abscissa denotes a supply ratio SR of the first source material to the second source material and the ordinate denotes an atomic content (at. %) of each of the germanium, the antimony and the tellurium components in the phase change material layer.

Referring to FIG. 7, the atomic content of germanium, antimony and tellurium vary with the were changed when the supply ratio SR of the first source material to the second source material is varied. For example, when the supply ratio SR varies from 1:0.5 to 1:1.5, the atomic content of the germanium decreases and the atomic content of the antimony increases.

In embodiments in which the germanium compound described above is used as a Ge precursor during formation of the phase change material layer, a maximum atomic content of the germanium in the phase change material layer can be about 40 at. %. In the conventional art, by contrast, it is difficult to form a phase change material layer having a germanium content greater than about 20 at. %. Using the germanium compound described herein, however, it is possible to form a phase change material layer having a high germanium content which is greater than about 20 at. % (e.g., about 40 at. %). Accordingly, phase change material layers having a wide range of germanium composition ratios can be formed. Therefore, it is possible to provide a specific phase change material layer which is suitable for a specific phase change memory device.

Figure 8A:
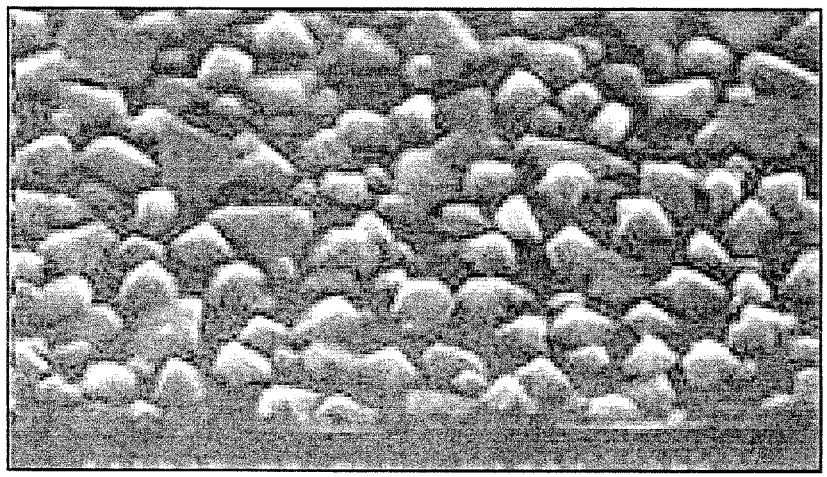
FIG. 8A is a scanning electron microscope (SEM) image of a conventional phase change material layer.
Figure 8B:
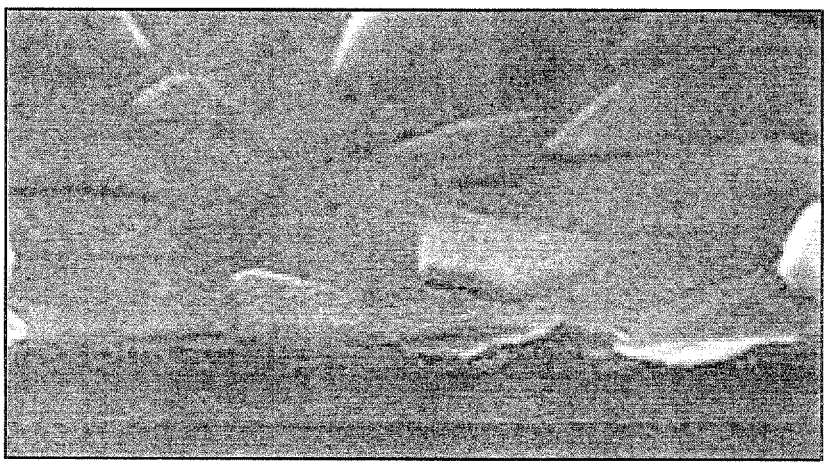
FIG. 8B is a scanning electron microscope image of a phase change material layer formed according to one embodiment.

FIG. 8A is a scanning electron microscope (SEM) image of a conventional phase change material layer and FIG. 8B is an SEM image of a phase change material layer formed according to one embodiment.

The conventional phase change material layer shown in FIG. 8A was formed using tetra allyl germanium (Ge($C_3H_5$)$_4$) as a Ge precursor, and the phase change material layer shown in FIG. 8B was formed using iso-propyl tris ethyl methyl amino germanium (Ge(iso-$C_3H_7$)(N($C_2H_5$)($CH_3$))$_3$) as a Ge precursor. As can be seen from FIGS. 8A and 8B, a surface of the phase change material layer formed according to the embodiments exemplarily described above is relatively more even (i.e., less rough) than a surface of the conventional phase change material layer.

According to the embodiments exemplarily described above, a Ge compound may be dissociated at a low temperature of about 350° C. or lower. In one embodiment, the Ge compound may be dissociated at a temperature ranging between about 250° C. and about 350° C. (e.g., about 325° C.). Accordingly, the Ge compound can be used to form a phase change material layer having a substantially uniform characteristic even when the phase change material layer is formed using a chemical vapor deposition (CVD) technique or an atomic layer deposition (ALD) technique. Further, the composition ratio of the phase change material layer can be easily controlled. Thus, it is possible to form various phase change material layers having diverse characteristics.

In addition, phase change material layers formed according to embodiments exemplarily described above may be uniformly formed at a low temperature of about 350° C. or lower, thereby filling an opening having a narrow width of about 100 nm or less. Accordingly, highly integrated phase change memory devices may be realized. Furthermore, power consumption of the phase change memory devices can be reduced because the phase change material patterns can be formed to have a narrow width of about 100 nm or less.

While the embodiments of the present invention have been exemplarily shown and described with reference to embodiments thereof, it will be understood by those of ordinary skill in the art that various changes in form and details may be made therein without departing from the spirit and scope of the present invention as defined by the following claims.

What is claimed is:

1. A germanium (Ge) compound having a chemical formula $GeR^1_xR^2_y$,
    wherein $R^1$ is an alkyl group and $R^2$ is an allyl group and a vinyl group,
    wherein x is greater than zero and less than 4, and
    wherein sum of x and y is equal to 4,
    with the proviso that $R^2$ does not comprise nitrogen.

2. The Ge compound of claim 1, wherein $R^1$ comprises iso-propyl.

3. A method of forming a semiconductor device, comprising:
    supplying a germanium precursor, an antimony precursor and a tellurium precursor to a substrate to form a phase change material layer,
    wherein the germanium precursor is a germanium compound having a chemical formula $GeR^1_xR^2_y$,
    wherein $R^1$ is an alkyl group,
    wherein $R^2$ is one of hydrogen, an allyl group and a vinyl group,
    wherein x is greater than zero and less than 4, and
    wherein the sum of x and y equal to 4,
    with the proviso that $R^2$ does not comprise nitrogen.

4. The method of claim 3, wherein $R^1$ comprises iso-propyl.

5. The method of claim 3, wherein the antimony precursor comprises tri iso-propyl antimony (Sb($C_3H_7$)$_3$).

6. The method of claim 3, wherein the tellurium precursor comprises tert butyl tellurium (Te($C_4H_9$)$_2$).

7. The method of claim 3, wherein supplying the germanium precursor, the antimony precursor and the tellurium precursor comprises:
    supplying a first source material; and
    supplying a second source material,
    wherein the first source material comprises the germanium and tellurium precursors and wherein the second source material comprises the antimony and tellurium precursors.

8. The method of claim 7, further comprising periodically supplying the first and second source materials.

9. The method of claim 7, further comprising alternately supplying the first and second source materials.

10. The method of claim 3, further comprising:
    forming an insulating layer on the substrate before forming the phase change material layer, wherein the insulating layer has an opening therein; and
    forming the phase change material layer in the opening.

11. The method of claim 10, wherein the opening has a width of about 100 nm or less.

12. The method of claim 10, further comprising forming a conductive plug in the opening before forming the phase change material layer.

13. The method of claim 3, further comprising forming the phase change material layer by performing a chemical vapor deposition process or an atomic layer deposition process at a process temperature of about 250° C. to about 350° C.

14. The method of claim 13, wherein the process temperature is equal to or lower than about 325° C.

* * * * *